(12) United States Patent
Park (10) Patent No.: US 7,863,898 B2
(45) Date of Patent: Jan. 4, 2011

(54) METHOD AND MAGNETIC RESONANCE SYSTEM TO DETERMINE THE PHASE POSITION OF A MAGNETIZATION

(75) Inventor: Jaeseok Park, Seoul (KR)

(73) Assignee: Siemens Aktiengesellschaft, Munich (DE)

( * ) Notice: Subject to any disclaimer, the term of this patent is extended or adjusted under 35 U.S.C. 154(b) by 92 days.

(21) Appl. No.: 12/402,946

(22) Filed: Mar. 12, 2009

(65) Prior Publication Data

US 2009/0230957 A1 Sep. 17, 2009

(30) Foreign Application Priority Data

Mar. 13, 2008 (DE) .................. 10 2008 014 060

(51) Int. Cl.
*G01V 3/00* (2006.01)
(52) U.S. Cl. ...................... 324/309; 324/307
(58) Field of Classification Search ......... 324/300–322; 600/407–445
See application file for complete search history.

(56) References Cited

U.S. PATENT DOCUMENTS

| | | | |
|---|---|---|---|
| 4,868,501 A | 9/1989 | Conolly | |
| 6,518,757 B1 | 2/2003 | Speier | |
| 6,809,518 B2 * | 10/2004 | Beaudoin et al. | 324/314 |
| 6,853,190 B2 * | 2/2005 | Nittka et al. | 324/309 |
| 7,274,190 B2 | 9/2007 | Harvey | |
| 7,390,671 B2 * | 6/2008 | Eliav et al. | 436/173 |
| 7,408,345 B2 * | 8/2008 | Bammer et al. | 324/307 |
| 7,787,930 B2 * | 8/2010 | Nezafat et al. | 600/410 |
| 2003/0234647 A1 | 12/2003 | Beaudoin et al. | |
| 2005/0024052 A1 | 2/2005 | Bendall et al. | |
| 2007/0229071 A1 * | 10/2007 | Heid | 324/309 |
| 2008/0287773 A1 * | 11/2008 | Harvey et al. | 600/412 |
| 2009/0146660 A1 * | 6/2009 | Schnell et al. | 324/318 |

FOREIGN PATENT DOCUMENTS

WO WO 96/10756 4/1996

OTHER PUBLICATIONS

"A Reduced Power Selective Adiabatic Spin-Echo Pulse Sequence," Conolly et al, Magnetic Resonance In Medicine, vol. 18, (1991) pp. 28-38.

* cited by examiner

*Primary Examiner*—Brij B Shrivastav
(74) *Attorney, Agent, or Firm*—Schiff Hardin LLP

(57) ABSTRACT

In a method to determine a phase position of a magnetization that is caused by radiation of an adiabatic RF pulse for the acquisition of magnetic resonance signals from a slice of an examination subject, an RF pulse of a first type is radiated and a first magnetic resonance signal is acquired, an adiabatic RF pulse is radiated and a second magnetic resonance signal is acquired, the phase of a magnetization induced by the RF pulse of the first type is calculated, as a first phase, and the phase of a magnetization induced by the adiabatic RF pulse is calculated as a second phase, and the phase position of the second phase in relation to the first phase is determined.

24 Claims, 5 Drawing Sheets

METHOD AND MAGNETIC RESONANCE SYSTEM TO DETERMINE THE PHASE POSITION OF A MAGNETIZATION

BACKGROUND OF THE INVENTION

1. Field of the Invention

The present invention concerns a method to determine the phase position of a magnetization, as well as a magnetic resonance system to implement such a method.

2. Description of the Prior Art

Magnetic resonance tomography is a widespread method to acquire medical image data of a subject to be examined. The subject to be examined is introduced into an optimally homogenous, static magnetic field ($B_0$ field). To acquire image data, magnetic gradient fields are applied and electromagnetic radio-frequency (RF) pulses are radiated that excite nuclear spins that precess around the magnetic fields. The magnetic flux density of the RF pulses is often designated $B_1$. Upon excitation with RF pulses, the direction of the magnetization that is originally aligned parallel to the $B_0$ field is tilted relative to this by a predetermined angle (flip angle). The flip angle depends both on the radiation duration of the RF pulse and on the $B_1$ field strength. For example, given a flip angle of 90°, a transverse magnetization (perpendicular to the $B_0$ field) can be generated, the decay of which is subsequently acquired as a magnetic resonance signal. To generate qualitatively high-grade image data, it is consequently desirable to obtain an optimally uniform deflection of the magnetization across a slice of the subject to be examined.

With the use of conventional RF pulses, $B_1$ inhomogeneities within a slice can occur, in particular due to an inhomogeneous penetration behavior in dielectric media (for example human or animal tissue). This leads to a non-uniform signal intensity and thus to a non-uniform contrast, particularly at high field strengths. In order to solve this problem, various $B_1$-insensitive, selective RF pulses have been developed. A precise slice selection can be achieved with composite adiabatic pulses. For specific imaging sequences, however, the use of adiabatic RF pulses is problematic since the magnetization generated by the pulses has an unknown phase position. It is necessary to know the phase position for the radiation of the refocusing pulses, in particular for multi-echo sequences (for example a turbo spin echo sequence).

The problem of the unknown phase position is solved in a conventional magnetic resonance method by replacing an adiabatic excitation pulse of an adiabatic excitation sequence with a conventional 90° excitation pulse, as described in Conolly et al., Magn Reson Med 1991; 18(1):28-38. The problem of the $B_1$ field inhomogeneity occurs, however, for this first pulse, which leads to an inhomogeneous exposure of the volume to be examined, and therefore in turn to a non-uniform signal intensity. An additional approach is the prediction of the RF-dependent phase by simulation of the Bloch equations for the composite adiabatic RF pulses. However, the phase is sensitive to $B_0$ inhomogeneities. If this technique is used with turbo/fast spin echo sequences, the signal decreases. The use of adiabatic RF pulses for a multi-echo imaging sequence is thus likewise not enabled by this method. In particular, for the fulfillment of a Car-Purcell-Meiboom-Gil (CPMG) condition in a multi-echo imaging sequence, it is necessary to know the orientation of the magnetization after excitation since this should coincide with the magnetic field axis of refocusing pulses.

SUMMARY OF THE INVENTION

An object of the present invention is to provide a method to determine the phase position of a magnetization that was caused by an adiabatic pulse, as well as to provide a magnetic resonance system to implement such a method.

This object is achieved in accordance with the invention by a method to determine the phase position of a magnetization wherein the acquisition of magnetic resonance signals from a slice of an examination subject is implemented by radiation of an adiabatic RF pulse, and further including radiation of an RF pulse of a first type and acquisition of a first magnetic resonance signal, radiation of an adiabatic RF pulse and acquisition of a second magnetic resonance signal, calculation of the phase of the magnetization induced by the RF pulse of a first type as a first phase, and calculation of the phase of the magnetization induced by the adiabatic RF pulse as a second phase, and determination of the phase position of the second phase in relation to the first phase. The phase caused by the adiabatic RF pulse thus can be determined relative to the phase of the magnetization caused by the RF pulse of the first type by the use of two different RF pulses. The pulses can be radiated in phase. For example, the RF pulse of the first type can be a sinusoidal RF pulse. Such pulses are used as excitation pulses in conventional magnetic resonance methods, for example, wherein different flip angles are achieved depending on the radiation duration and field strength. For such pulses, the phase position of the excited magnetization is normally known relative to the phase of the radiated RF pulse. With the use of a sinusoidal RF pulse, for example, the CPMG condition can be satisfied in a multi-echo sequence. By determining the phase position of the second phase (that was induced by the adiabatic RF pulse) in relation to the first phase, it is thus possible to conduct a compensation for the phase position and also to satisfy a CPMG condition given excitation via an adiabatic RF pulse. The phase of the magnetization normally corresponds to the transversal magnetization, thus the component perpendicular to the $B_0$ direction. For example, the use of an adiabatic excitation pulse in a multi-echo imaging sequence is thereby enabled.

According to an embodiment of the invention, the adiabatic RF pulse has an adiabatic half-passage pulse (AHP pulse). For example, such a pulse can be used in order to slew the magnetization that is essentially aligned along the $B_0$ direction by 90° into the transverse plane. One advantage of the use of an AHP pulse is that the stewing of the magnetization is essentially insensitive to $B_1$ inhomogeneities. The adiabatic half-passage pulse can be radiated as a non-slice-selective RF pulse. For example, the AHP pulse can be radiated without the application of magnetic field gradients.

According to a further embodiment of the invention, the adiabatic RF pulse is formed by two adiabatic full-passage pulses (AFP pulses). The AFP pulses can be used to generate a spin echo signal, for example. For example, the two AFP pulses can be radiated such that they exhibit a self-refocusing effect, so no rephasing gradient is necessary in the acquisition of a spin echo magnetic resonance signal. Furthermore, the adiabatic full-passage pulse can be radiated while a slice selection gradient is present. A slice selection gradient is a magnetic field gradient that is applied, for example, in the direction of the $B_0$ field (z-direction). For example, such a slice selection gradient can interact with the AFP pulses such that the magnetization is deflected essentially by 180° only in one slice of the subject to be examined. A slice-selective acquisition of magnetic resonance signals can thus ensue.

According to another embodiment of the invention, the method furthermore includes radiation of an additional adiabatic RF pulse an acquisition of a third magnetic resonance signals. The calculation of the first phase and second phase can then ensue on the basis of the second and third magnetic resonance signal. Instead of the additional adiabatic RF pulse, for example, an RF pulse of the first type can be radiated. The acquisition of two magnetic resonance signals that were caused by similar excitation pulses has the advantage that an additional phase shift can also be determined that is based on a resonance frequency shift. Such a resonance frequency shift can be caused by magnetic field inhomogeneities, for example.

In a further embodiment of the invention, the adiabatic pulse is designed such that a spin echo signal is generated. For example, the adiabatic pulse can be a composite adiabatic pulse formed by one AHP and two AFP pulses. Adiabatic pulses of different composition that can cause a spin echo signal are also possible. Such pulses enable a $B_1$ field-insensitive excitation with simultaneous slice selectivity. With excitation with an adiabatic RF pulse that generates a spin echo signal, the second and third magnetic resonance signal can be acquired with different echo times, for example. With different echo times, a resonance frequency shift can induce a different, additional phase, so a determination of the resonance frequency shift can ensue. The calculation of the first and second phases can be a calculation of a resonance frequency shift on the basis of the different echo times and the phase of the acquired second and third magnetic resonance signals. The phase position thus can be reliably determined even with an existing magnetic field inhomogeneity. For example, the difference between the phase of the acquired magnetic resonance signal and the phase induced by tile RF pulses of the magnetization can be calculated.

In another embodiment of the invention, the calculation of the first phase and/or of the second phase is a phase reconstruction. This is advantageously implemented in regions in which phase jumps of a predetermined magnitude are discovered between two adjacent data points. For example, in the acquisition of frequency-coded magnetic resonance signals a phase can be calculated for every point in image space, wherein the value range for the phase essentially extends over a range from −180° to +180°. If the phase shift exceeds this value range, the calculated phase at this point makes a jump due to the periodicity, which jump can be discovered and remedied via reconstruction. Such a phase reconstruction (or phase unwrapping) is known to those skilled in the art and therefore need not be discussed in detail herein. The phase reconstruction advantageously occurs only in regions with a predetermined signal intensity in image space. Acquired magnetic resonance signals can be represented as image data by Fourier transformation, with which the intensity value of the pixels is linked with the signal amplitude of the acquired magnetic resonance signals. For example, for the phase reconstruction only regions wherein the signal intensity lies above a predetermined threshold are taken into account. This is advantageous since image data points from other regions normally correspond to those regions of the examination subject in which only an insignificant magnetization has occurred. A magnetization phase in these regions is consequently essentially undefined, and a phase reconstruction in these regions would consequently be less meaningful.

In another embodiment of the invention, the magnetic resonance signals are acquired while a gradient is present in the axial direction. For example, each of the first, the second and the third magnetic resonance signals are acquired while the gradient is present. A frequency coding of the magnetic resonance signals thus ensues, so a reconstruction of the axial position is enabled. No additional magnetic field gradients are applied, which is advantageous. In this case, projection data are acquired in the transverse directions, i.e. x-direction and y-direction perpendicular to the axial $B_0$ field direction (z-direction).

According to a further embodiment, the phase position is determined for various axial positions in the slice form which the magnetic resonance signals are acquired. For example, if RF pulses for refocusing are subsequently radiated, these RF pulses normally have multiple frequencies in order to achieve an optimally uniform excitation across a predetermined slice thickness. It is thus advantageous for the phase position to be determined for various axial positions, for example, correspond to the different RF sequences given an application of a slice selection gradient.

According to another embodiment of the present invention, a rephasing gradient and a pre-phasing gradient are applied in the axial direction before the acquisition of the first magnetic resonance signal. It is thereby ensured that the phase of the magnetization (which phase is impressed by a slice detection gradient that is advantageously applied during the radiation of the RF pulse) will be compensated by means of the rephasing gradient. By using a pre-phasing gradient, the magnetization is caused to be essentially in phase across the slice thickness in the acquisition of the first magnetic resonance signal, during which a slice selection gradient is advantageously applied in the axial direction. The first magnetic resonance signal is advantageously acquired following a gradient echo sequence. The phase of the magnetization is essentially defined by the excitation pulse (RF pulse of the first type) through such a procedure. The resonance frequency shift, as mentioned above, can have an additional influence on the phase of the magnetization.

According to another embodiment of the present invention, a multi-echo magnetic resonance sequence that includes at least one adiabatic RF pulse is executed following the determination of the phase position. For example, an adiabatic RF pulse composed of one AHP pulse and two AFP pulses is used to generate a transversal magnetization. The phase of refocusing pulses of the multi-echo magnetic resonance sequence can thereby be established under consideration of the determined phase position. It is therefore furthermore advantageous for the establishment of the phase to ensue dependent on frequency. A $B_1$-insensitive excitation of the nuclear spins in a slice of the examination subject thus can ensue. A homogenous exposure of the examined volume is achieved with such an excitation, wherein (based on the knowledge of the phase position of the generated magnetization) refocusing pulses can subsequently be radiated such that a phase condition of the multi-echo imaging sequence is satisfied. For example, the determined phase position is used to satisfy a CPMG condition of a multi-echo imaging sequence. The multi-echo magnetic resonance frequency can be a turbo spin echo sequence for imaging, for example. To satisfy the CMPG condition, the magnetic field vector of the radiated RF refocusing pulses should coincide with the spin orientation after excitation, for example. This can be achieved by the phase position that is generated by the excitation with adiabatic RF pulses being compensated upon radiation of the RF refocusing pulses. This enables the advantages of an adiabatic, selective excitation—for example the $B_1$-insensitivity—also to be utilized in multi-echo imaging. The method can also be used for other applications in which compensation of a phase position caused by adiabatic excitation is necessary.

Furthermore, the invention encompasses a magnetic resonance system that is designed to determine the phase position of a magnetization caused by radiation of an adiabatic RF pulse for the acquisition of magnetic resonance signals from a slice of an examination subject. The magnetic resonance system includes an acquisition unit to radiate RF pulses in a region of the examination subject and to acquire magnetic resonance signals from this region and a control unit that is designed to control the acquisition unit by causing radiation of an RF pulse of the first type and acquisition of a first magnetic resonance signal, and radiation of an adiabatic RF pulse and acquisition of a second magnetic resonance signal. The system further includes a calculation unit designed to calculate, as a first phase, the phase of the magnetization induced by the RF pulse of the first type, and to calculate as a second phase, of the phase of the magnetization induced by the adiabatic RF pulse, and to determine the phase position of the second phase in relation to the first phase. With such a magnetic resonance system the phase position after adiabatic excitation can be established, for example, wherein compensation for the specific phase position in an imaging with a multi-echo magnetic resonance sequence with adiabatic excitation is particularly advantageous. A homogenous exposure and therefore a uniform contrast are thus also enabled for a multi-echo imaging sequence.

The control unit can furthermore be designed to control the acquisition unit to radiate an additional adiabatic RF pulse and to acquire a third magnetic resonance signal, and the computer is designed to calculate the first phase and the second phase on the basis of the first, second and third magnetic resonance signals. Furthermore, a resonance frequency shift that is caused, for example, by inhomogeneous magnetic fields, can be determined with a magnetic resonance system of such a design. A precise calculation of the phase position is enabled.

Furthermore, the magnetic resonance system can be designed to implement a method described above. For example, the magnetic resonance system is designed to radiate an adiabatic half-passage pulse or an adiabatic full-passage pulse, as well as to apply magnetic field gradients in the axial direction. It can be designed to calculate a resonance frequency shift and to execute multi-echo magnetic resonance sequences for imaging.

Furthermore, the invention encompasses a computer-readable mechanism encoded with programming instructions which, upon execution in a computer functionally connected with a magnetic resonance system, cause the system to execute a method as described above. For example, the computer program can initiate the radiation of an RF pulse of the first type or of an adiabatic RF pulse, as well as the acquisition of first and second magnetic resonance signals, and a determination of the phase position of the magnetization induced via the adiabatic RF pulse.

The computer can be part of the magnetic resonance system, for example in the form of the aforementioned computer unit, but it can alternatively be connected with the magnetic resonance system via a network connection, for example.

DESCRIPTION OF THE PREFERRED EMBODIMENTS

Figure 1:
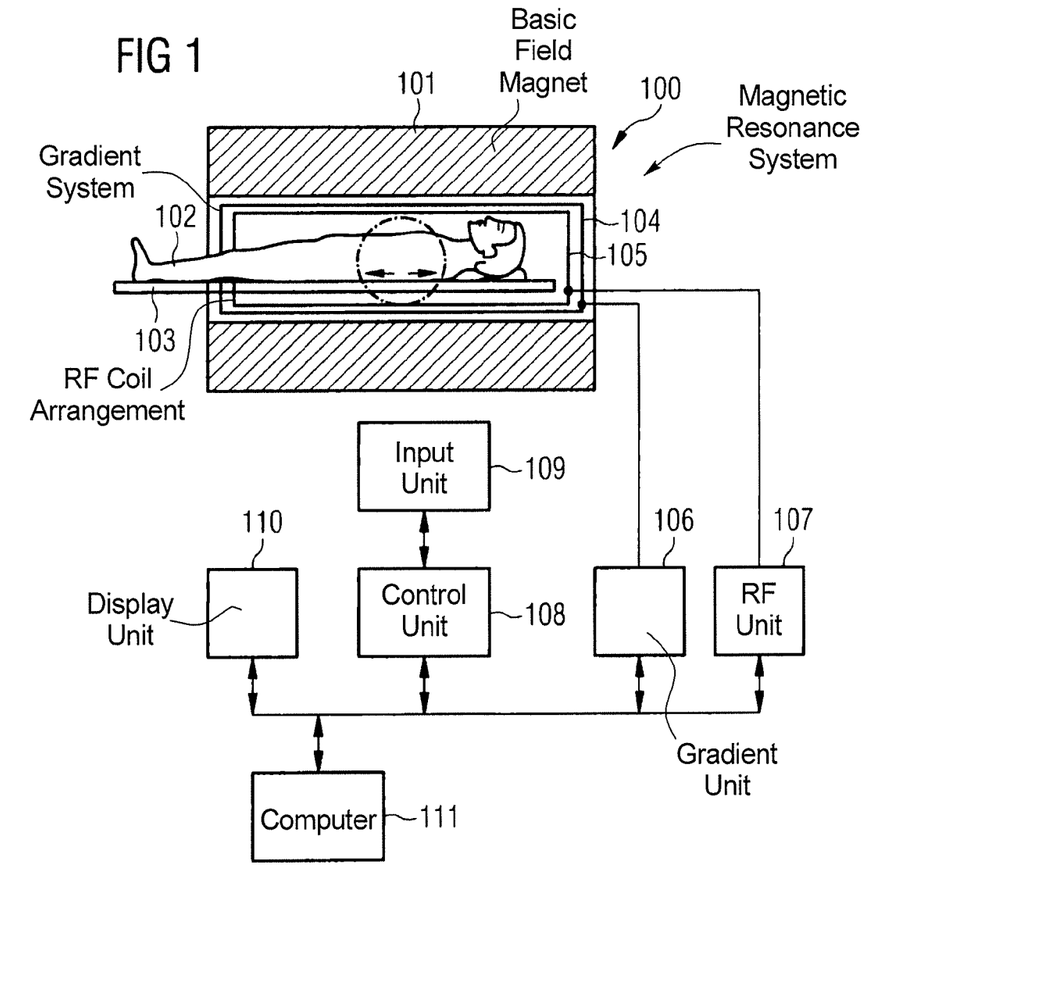
FIG. 1 is a schematic representation of a magnetic resonance system according to an embodiment of the invention.

FIG. 1 schematically shows a magnetic resonance system 100 with which the phase position of a magnetization induced by an adiabatic radio-frequency pulse can be determined, for example for a subsequent acquisition of image data with a multi-echo magnetic resonance sequence. Such a magnetic resonance system has a basic field magnet 101 for generation of a polarization field $B_0$. In the example shown, the examination subject is an examination person (subject) 102 who is arranged on a bed 103. As is schematically shown by arrows, the bed can be driven into the magnet 101 and be moved therein. The magnetic resonance system furthermore has a gradient system 104 to generate magnetic field gradients that are used for the imaging and spatial coding. To excite the polarization resulting in the basic magnetic field, a radio-frequency (RF) coil arrangement 105 is provided that radiates a radio-frequency field into the examination person 102 in order to deflect the magnetization from the equilibrium position. To control the magnetic field gradients, a gradient unit 106 is provided, and an RF unit 107 is provided to control the radiated RF pulses. A control unit 108 centrally controls the magnetic resonance system; the selection of the imaging sequences likewise ensues in the control unit 108. An operator can select a sequence protocol via an input unit 109 and make additional adjustments to the magnetic resonance system, for example the specifications of imaging parameters. A display unit 110 serves to display acquired magnetic resonance signals or reconstructed image data as well as the adjusted parameters and other graphics required for operation of the magnetic resonance system. Furthermore, a computer 111 is provided that, for example, serves for reconstruction of image data from acquired magnetic resonance signals or to calculate the phase position (as is explained in detail in the following). The general mode of operation of a magnetic resonance system is known to those skilled in the art, such that a detailed description of the general components is not needed herein.

The acquisition unit of the magnetic resonance system 100 can include, for example, the gradient unit 106, the gradient system 104, the RF unit 107, the radio-frequency coil arrangement 105 and the magnet 101. Additional embodiments of the acquisition unit are naturally conceivable, for example the use of special head coils, chest coils and other local coil arrangements for radio-frequency trans and reception operation, the use of, different gradient coils for the gradient system, and the use of different magnets 101, for example permanent magnets, normally-conducting or superconducting magnets. The control unit 108 controls the gradient unit 106 and the RF unit 107 such that a first radio-frequency excitation pulse that generates a magnetization with known phase position is radiated into the examination region. The decay of the magnetization created by the excitation is subsequently likewise acquired with the use of the radio-frequency coil arrangement 105 and the RF unit 107. Magnetic field gradients can be applied during these procedures by controlling the gradient unit 106, for example during the radiation of the RF pulses or during the acquisition of magnetic resonance signals. Magnetic field gradients can be applied in different directions with the gradient system 104, for example for slice selection, phase coding or frequency coding, as well as what are known as spoiler or crusher gradients that serve to destroy a remaining magnetization and the decay signal (free induction decay, FID). For example, a detected induction signal can be digitized by an analog-to-digital converter (not shown) and subsequently be processed by the computer 111. The control unit 108 furthermore controls the RF unit 107 such that an adiabatic radio-frequency pulse that consists of one adiabatic half-passage pulse and two adiabatic full-passage pulses is radiated into the examination region. Following this, a magnetic resonance signal is again acquired with the radio-frequency coil arrangement 105 and the RF unit 107, wherein a gradient in the axial direction (slice selection gradient) is applied by means of the gradient unit 106. Acquired magnetic resonance signals can then be processed in the computer 111. The computer 111 is designed such that it can calculate from the acquire magnetic resonance signals the relative phase position between the magnetization that was induced by the first excitation pulse and the magnetization that was induced by the radiated adiabatic excitation pulse. The control unit 108 can then use this information to establish the relative phase between excitation pulses to be radiated. For example, the control unit 108 can initiate the radiation of a composite adiabatic excitation pulse with predetermined phase during the execution of a turbo spin echo sequence, and control the subsequent radiation of a predetermined number of refocusing pulses (likewise with predetermined phase) and the acquisition of induced spin echo signals. Upon establishing the phase of the refocusing pulses, the control unit 108 uses the relative phase calculated by the computer 111 in order to compensate for the phase position induced by the adiabatic excitation pulse.

In multi-echo magnetic resonance sequences, for example the turbo spin echo sequence, 180° pulses are used for refocusing. If the deflection of the magnetization does not amount to a full 180°, which can rarely be reached, the deviation is cumulative, which can lead to significant variations of the amplitude of acquired magnetic resonance signals during the turbo spin echo sequence. This can be avoided by satisfying the Car-Purcell-Meiboom-Gil (GPMG) condition. The phase of 180° refocusing pulses is hereby offset by 90° counter to the 90° excitation pulse. A cumulative deviation is thus avoided. Given a radiation of the RF pulses under this condition, all even echoes show the correct amplitude while the odd echoes exhibit a somewhat reduced amplitude. In the magnetic resonance system 100 described here, the computer 111 and the control unit 108 are designed such that the phase position of the magnetization is determined after excitation, and thus the CPMG condition can be satisfied upon radiation of the refocusing pulses. Magnetic resonance signals with correct amplitude can thus be acquired by the magnetic resonance system 101. The acquisition of magnetic resonance data is furthermore $B_1$-insensitive due to the use of the composite adiabatic excitation pulse. The magnetic resonance system described herein thus enables the acquisition of image data with improved quality and homogenous contrast.

Figure 2:
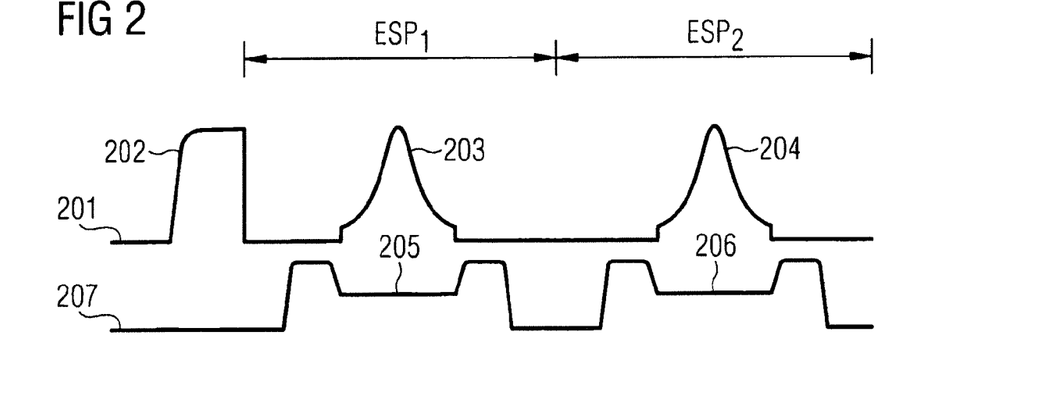
FIG. 2 is a schematic representation of an adiabatic RF pulse that is composed of one adiabatic half-passage pulse and two adiabatic full-passage pulses.

FIG. 2 schematically shows a composite adiabatic excitation pulse. An adiabatic radio-frequency pulse is generally a pulse that possesses an amplitude modulation and a frequency (or phase) modulation. An adiabatic pulse is normally designed to excite all hydrogen spins of a sample with a common precision.

The excitation of the nuclear spins is thereby essentially $B_1$-insensitive beyond a certain threshold of the $B_1$ field strength, so a common excitation of the nuclear spins can be achieved even in the presence of magnetic field inhomogeneities.

The sequence of the RF pulses is shown on axis 201. The composite adiabatic pulse from FIG. 2 consists of one adiabatic half-passage (AHP) pulse 202 followed by two adiabatic full-passage (AFP) pulses 203 and 204. The AHP pulse 203 produces a rotation of the magnetization by 90°. No gradient is applied during the radiation of the AHP pulse 202 and the excitation does not ensue in a slice-selective manner. Axial gradients 205 and 206 are applied during the radiation of the AFP pulses 203 and 204. These are shown on the axis 207 and are often also designated as slice selection gradients. Adiabatic full-passage pulses produce a rotation of the magnetization by essentially 180°. This excitation of the magnetization thereby ensues in a slice-selective manner. Frequency-selective adiabatic pulses can be obtained via a limitation of the pulse bandwidth, for example. Hyperbolic secant (sech) pulses (~1/cosh x) can be used as slice-selective AFP inversion pulses. The application of the slice selection gradients 205 and 206 leads to different Larmor frequencies of the excited spins, whereby again only spins from a predetermined slice are excited due to the frequency selectivity of the adiabatic pulses 203 and 204. For example, the 180° AFP pulses 203 and 204 lead to a spin echo sequence after a time duration $ESP_1+ESP_2$. In general, the point in time at which a spin echo can be observed depends on the time interval between the excitation pulse (AHP) and the refocusing pulse (here AFP 203 or AFP 204). The composite adiabatic RF pulse shown here is $B_1$-insensitive. Furthermore, a slice selection with high precision is possible with such a pulse; it also provides for a good exposure or introduction of the RF energy into the slice to be examined, as well as for a suppression of signals that have their origin outside of the predetermined slice. However, in particular the AHP pulse induces a radio-frequency-dependent phase position of the magnetization. This can destroy the CPMG condition of a turbo spin echo sequence, which leads to a signal loss or artifacts of image data. The composite adiabatic RF pulse described here can be used with the method according to the invention. However, it should be clear that a number of additional composite adiabatic pulses can be constructed, and that these can also be used with the described invention. For example, an adiabatic pulse with one AHP pulse and one AFP pulse can be used, or more than two AFP pulses can be provided. Furthermore, a combination of conventional (for example sinc) pulses with adiabatic pulses is also conceivable. Such a composite adiabatic excitation pulse can also comprise one or more AHP pulses, and magnetic field gradients can be applied in different directions upon radiation of the pulses.

Figure 3:
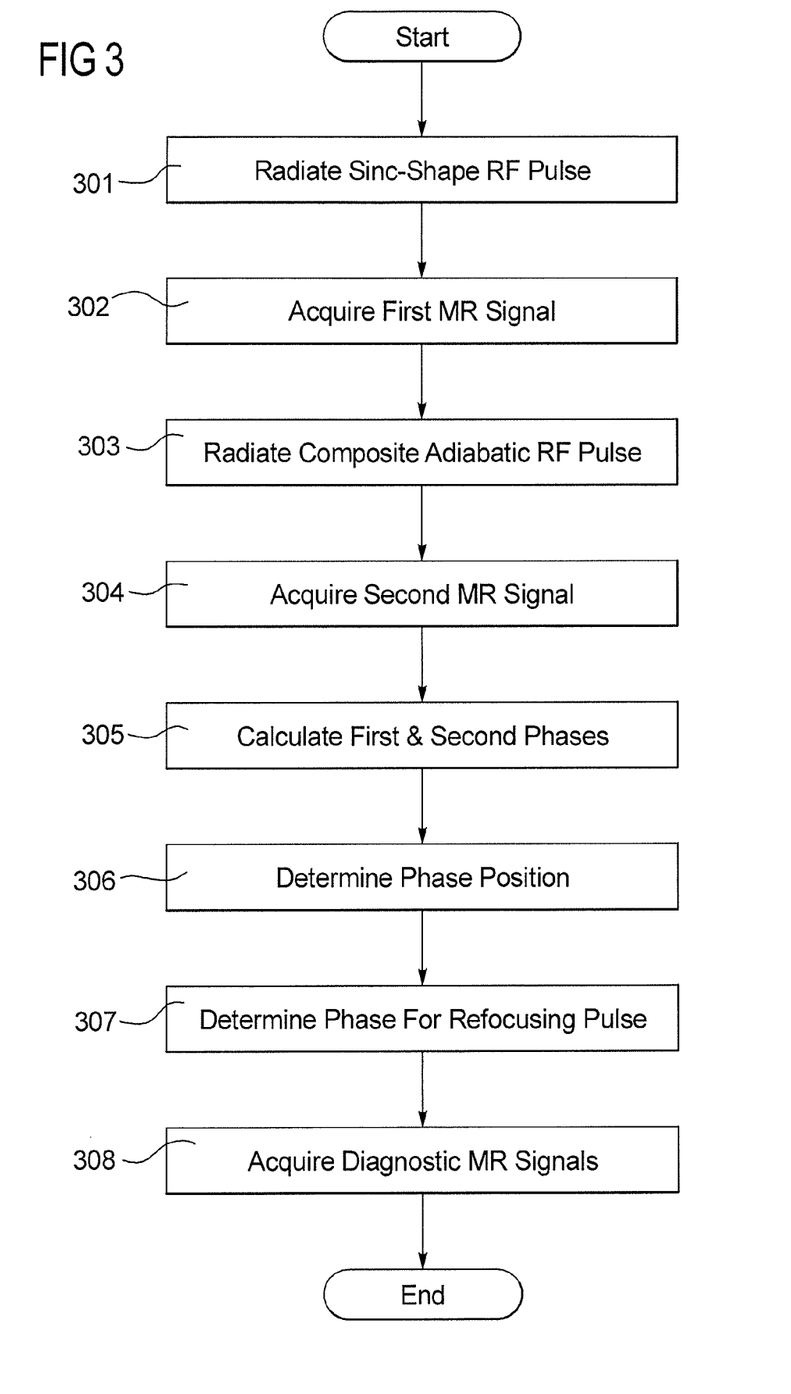
FIG. 3 is a flowchart of an embodiment of the method according to the invention to determine the phase position.

FIG. 3 shows a flow chart of an embodiment of the method according to the invention. In a first Step 301, a sinc-shaped RF pulse is radiated. Sinc-shaped RF pulses are known to those skilled in the art and need not be explained in detail herein. The sinc pulse here does not need to be a 90° excitation pulse; it can also deflect the magnetization by a smaller angle. Given a decay of the magnetization, a first magnetic resonance signal can be acquired in Step 302. The radiation and the acquisition are, for example, controlled by a control unit such as the control unit 108 of the magnetic resonance system 100. In a next Step 303, a composite adiabatic RF pulse is radiated. This RF pulse can be in phase with the sinc pulse. For example, the composite adiabatic RF pulse described in FIG. 2 can be used. A homogenous exposure of the selected slice of the examination subject is achieved with this pulse. The decay of the induced magnetization is detected in Step 304 via acquisition of a second magnetic resonance signal, for example in the form of a spin echo signal. The control of the radiation and acquisition can in turn ensue with a unit similar to the control unit 108. A first phase and a second phase are calculated in Step 305 based on the acquired magnetic resonance signals. The first phase is the phase of the magnetization that is induced by the sinc pulse. The second phase is the phase of the magnetization that was induced by the composite adiabatic RF pulse. The acquisition of the magnetic resonance signals advantageously ensues without an application of magnetic field gradients in the direction perpendicular to the axial direction. A magnetic field gradient in the axial direction is applied so that magnetic resonance signals with different frequencies are acquired that correspond to different axial positions within the detected slice. The phase position of the magnetization induced by the composite adiabatic RF pulse can now be determined in Step 306 by comparison of the determined first phase and second phase of the magnetization. The determination of the phase position advantageously ensues dependent on frequency. This is in particular achieved via the frequency coding with the use of the magnetic field gradients in the axial direction.

The phase for refocusing pulses is determined in Step 307 under consideration of the specific phase position. In particular the axis of the $B_1$ field of the refocusing pulses should coincide with the orientation of the magnetization after excitation to satisfy the CPMG condition. The phase for subsequent refocusing pulses can thus be established due to the knowledge of the phase position after excitation with the composite adiabatic RF pulse. The acquisition of diagnostic magnetic resonance signals follows in Step 308 with a multi-echo magnetic resonance sequence in which a composite adiabatic RF pulse is advantageously radiated for excitation and subsequent refocusing pulses are radiated with the phase established in Step 307 to generate spin echo magnetic resonance signals. The described method can be implemented with the magnetic resonance system shown in FIG. 1, for example. Due to the good exposure with the aid of the adiabatic excitation pulses, image data with homogenous contrast can be acquired with the method, wherein signal degradations as well as artifacts can be avoided by taking into account the determined phase position.

Figure 4:
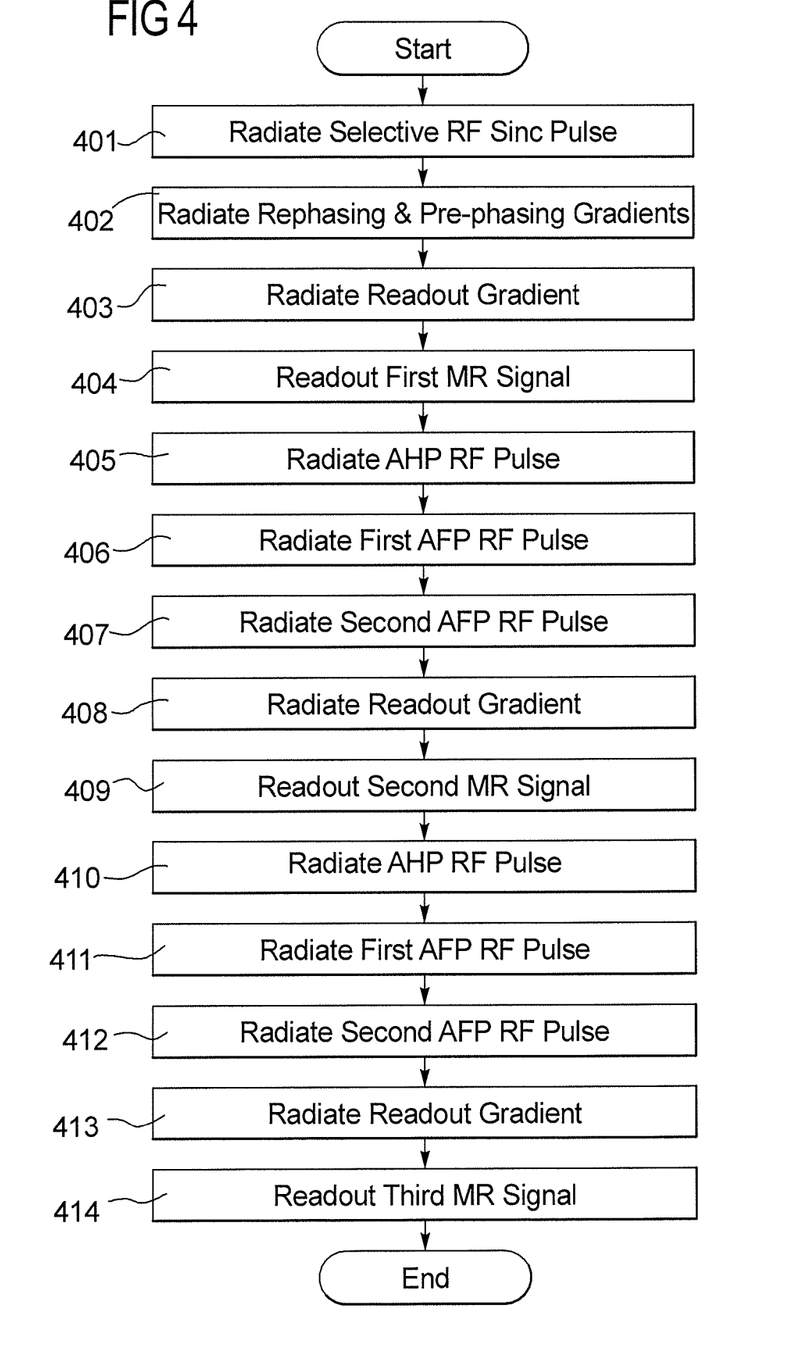
FIG. 4 is a flowchart of a method for acquisition of magnetic resonance signals for a phase calibration.
Figure 5:
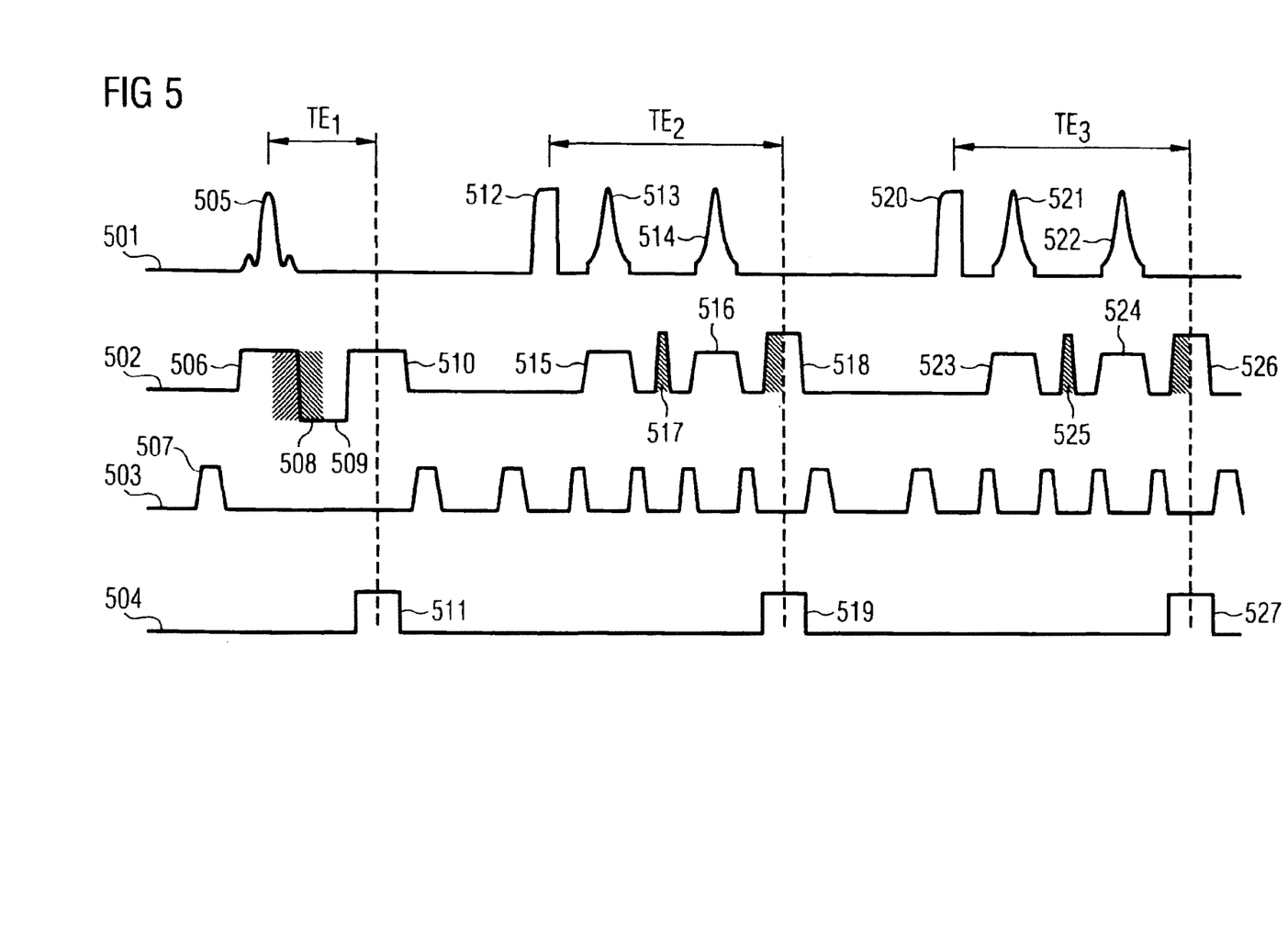
FIG. 5 is a schematic representation of the sequence of the radiation of RF pulses and the application of magnetic field gradients in an embodiment of the method according to the invention.

FIG. 4 shows a flowchart of an additional embodiment of the method according to the invention. FIG. 4 in particular describes more precisely the method steps of the radiation of RF pulses and the acquisition of magnetic resonance signals. The method steps of the method described in FIG. 4 are schematically shown in the form of a diagram as a function of time in FIG. 5. The RF pulse axis 501 shows the time sequence of the radiation of RF pulses. At which points in time gradients are applied in the axial direction is schematically presented on the z-gradient axis 502. The application of crusher gradients is schematically shown on the crusher gradient axis 503. At which points in time an analog-to-digital conversion ensues (thus at which points in time magnetic resonance signals are acquired) is shown on the ADC axis 504. It should be clear that FIG. 5 is only a schematic representation. The scaling in the direction of the time axis and of amplitudes of the RF pulses and gradients is only by way of example and can significantly deviate in an actual sequence for determination of the phase position. The sequence shown in FIG. 5 can also be designated as a "prescan" since it is normally executed before an imaging sequence (for example a turbo spin echo sequence) and essentially serves only to determine the phase position.

Referring to FIG. 4, an excitation with a selective sinc pulse ensues in a first Step 401. This excitation with a sinc pulse essentially serves as a reference since the phase position of the magnetization is generally known given such an excitation. After such an excitation, the phase difference between $B_1$ field and transversal magnetization is normally 90°. Since this essentially depends on the phases of the transversal magnetization, it is not necessary that the sinc pulse deflects the original magnetization parallel to $B_0$ by a full 90°; smaller flip angles, for example, 20°, are sufficient. A gradient is applied in a direction axial to the slice selection during the radiation. The application of a rephasing and pre-phasing gradient subsequently follows in Step 402. These essentially serve to compensate again for the phase differences between precessing spins along the axial direction that are induced by application of the slice selection gradients and a readout gradient in the axial direction. The application of the readout gradient in the z-direction follows in Step 403. The first magnetic resonance signal is read out in Step 404 while the readout gradient is applied. The readout ensues at a point in time $TE_1$ after the radiation of the sinc pulse. A sequence composed of Steps 401-404 can, for example, correspond to a gradient echo sequence, wherein here the gradients are applied in the axial direction. With reference to FIG. 5, the selective sinc pulse is identified with the reference character 505. The slice selection gradient is applied during the radiation of the sinc pulse 505. A crusher gradient 507 is applied before the deflection of the magnetization with the sinc pulse 505 and the slice selection gradient 506, which crusher gradient 507 dephases a possibly still-existing magnetization in order to prevent the occurrence of a resulting free induction decay signal. The crusher gradient axis 503 shows additional crusher gradients that should not be repetitively described in detail. The use of crusher gradients is known to those skilled in the art and thus need not be described in detail herein. Spins at various axial positions precess with different frequencies by the application of the slice selection gradients 506, whereby a phase of the magnetization that is dependent on the axial position is impressed. This is compensated with the rephasing gradient 508. The areas shaded in different directions thereby indicate that the moments of the gradients are equal. Since gradient 508 is applied in the opposite direction, the spins rephase. The pre-phasing gradient 509 is applied in turn in order to impress on the magnetization a dependency of the phase on the axial position so that the spins rephase again upon application of the readout gradient 510 in the opposite direction. A maximum magnetic resonance signal is thus acquired during the readout process. The acquisition of the magnetic resonance signal is indicated on the DAC axis 504 with the reference character 511. The acquisition generally ensues by an analog-to-digital conversion of the signal induced in an acquisition coil. The acquisition of the magnetic resonance signal ensues at a point in time $TE_1$ after the radiation of the sinc pulse 505. A dephasing of the spins can be caused by magnetic field inhomogeneities or the like during this time period. The phase of the magnetization that was induced by the sinc excitation pulse can then not be exactly reconstructed from the acquired magnetic resonance signals. The additional phase caused by the concomitant resonance frequency shift $\Delta\omega_0$ can be determined with the aid of the method described in the following. The phase of the magnetization that was induced by the sinc pulse 505 can thus be established using the acquired magnetic resonance signals, even given the presence of such a frequency shift.

Referring again to FIG. 4, the excitation now ensues with an adiabatic pulse that comprises AHP and AFP pulses. The excitation initially ensues with an adiabatic half-passage pulse in Step 405. A first adiabatic full-passage pulse is subsequently radiated in Step 406, followed by a second adiabatic full-passage pulse in Step 407. A readout gradient is subsequently applied in the z-direction (Step 408), during which a second magnetic resonance signal is read out in Step 409. The readout ensues at a point in time $TE_2$ after radiation of the adiabatic AFP pulse (Step 406).

In FIG. 5 it is clear that no gradient is applied in the axial direction while the AHP pulse 512 is radiated. The excitation by the AHP pulse 512 does not ensue selectively, wherein a frequency-dependent phase is impressed on the magnetization. This phase is generally not known and should be determined in relation to the phase of the magnetization after excitation with the sinc pulse 505. A slice selection ensues via radiation of the AFP pulse 513 with simultaneous application of the magnetic field gradient 515. While the magnetization (which is originally aligned essentially parallel to $B_0$) is essentially slewed 90° in the transversal plane by the AHP pulse 512, a deflection of the magnetization by essentially 180° ensues with the radiation of the RF pulse 513. A spin echo is thus generated only in the selected slice, in contrast to which the transversal magnetization decays in other regions of the examination subject. A slice selection gradient 516 is similarly applied during the radiation of the AFP pulse 514. The same slice is advantageously selected with the slice selection gradients 515 and 516 as was selected with the slice selection gradient 506. Furthermore, a pre-phasing gradient 517 is applied. This in turn serves to compensate the dephasing that is caused in the axial direction by the readout gradient 518. In particular, via the pre-phasing gradient 517 it is achieved that the spins in the axial direction rephase at the point in time of the acquisition of the magnetic resonance signal, such that a maximum signal can be acquired. Gradient moments that cancel each other out are in turn marked with regions shaded in opposite directions. Due to the inversion pulse 514, the pre-phasing gradient 517 is applied in the same direction as the readout gradient 519. The acquisition of the magnetic resonance signal 519 ensues as mentioned at the point in time $TE_2$, after the radiation of the AHP pulse 512. Refocusing gradients are not necessary for the slice selection gradients 515 and 516 since the pulses are self-refocusing. A spin echo signal is acquired at a point in time $TE_2$. Since neither a phase coding nor a frequency coding has occurred in the x- or y-direction, projection data for these two directions are acquired. As already mentioned, a frequency coding ensues in the axial direction. The phase of the magnetization that was induced by the composite adiabatic RF pulse can now be determined from the acquired magnetic resonance signals. However, an additional phase contribution can occur, for example due to inhomogeneities in the magnetic field and shifts of the resonance frequency that therefore result. However, this additional dephasing occurs only during a time $T_{AHP}/2$ since the rephasing is canceled during the remaining time due to the dephasing properties of the 180° AFP pulses. The time sequence of the AFP pulses 513 and 514 is correspondingly established so that a cancellation of the dephasing by $\Delta\omega_0$ occurs.

As described in the following, the phase portion of the frequency shift can, for example, be determined by a radiation of an additional composite adiabatic excitation pulse and via acquisition of additional magnetic resonance signals. Referring to FIG. 4, an additional excitation ensues with an adiabatic half-passage pulse in Step 410 and a radiation of a first AFP pulse (Step 411) and a second AFP pulse (Step 412). A readout gradient is applied in the z-direction in Step 413, wherein the readout of a third magnetic resonance signal ensues again in Step 414 while the readout gradient is applied. However, the readout now ensues at a point in time $TE_3$ after the excitation with the AHP pulse in Step 410. The radiation of the AHP pulse 520 and of the AFP pulses 512 and 522 is shown in FIG. 5. However, the temporal arrangement of these pulses differs from that of the pulses 512-514. In particular, the pulses are arranged such that a dephasing due to the resonance frequency shift is not completely compensated. For example, an additional dephasing is generated by an additional dephasing duration between the pulses. The phases that are present after excitation with the pulses 512-514 and 520-522 differ due to these additional phases. The phase induced by the resonance frequency shift $\Delta\omega_0$ can be established from this phase difference. Moreover, the sequences of the first and second adiabatic excitation resemble one another. In particular, slice selection gradients 523 and 524 as well as a pre-phasing gradient 525 are applied in turn. The acquisition of magnetic resonance signals 527 ensues during the readout gradient 526. Relaxation times can respectively be provided between sinc excitation, the first adiabatic excitation and the second adiabatic excitation. Furthermore, these three excitation pulses can be radiated in phase. The magnetic resonance signals acquired with such an acquisition sequence enable the determination of the phase position that was impressed on the magnetization by the adiabatic excitation pulse. It should again be understood that such a prescan can also comprise additional or different excitations. For example, two sinc excitations with subsequent acquisition of magnetic resonance signals could also be contained, for example to determine the phase induced by the resonance frequency shift. The determination of the phase position is subsequently explained precisely with reference to FIG. 6.

Figure 6:
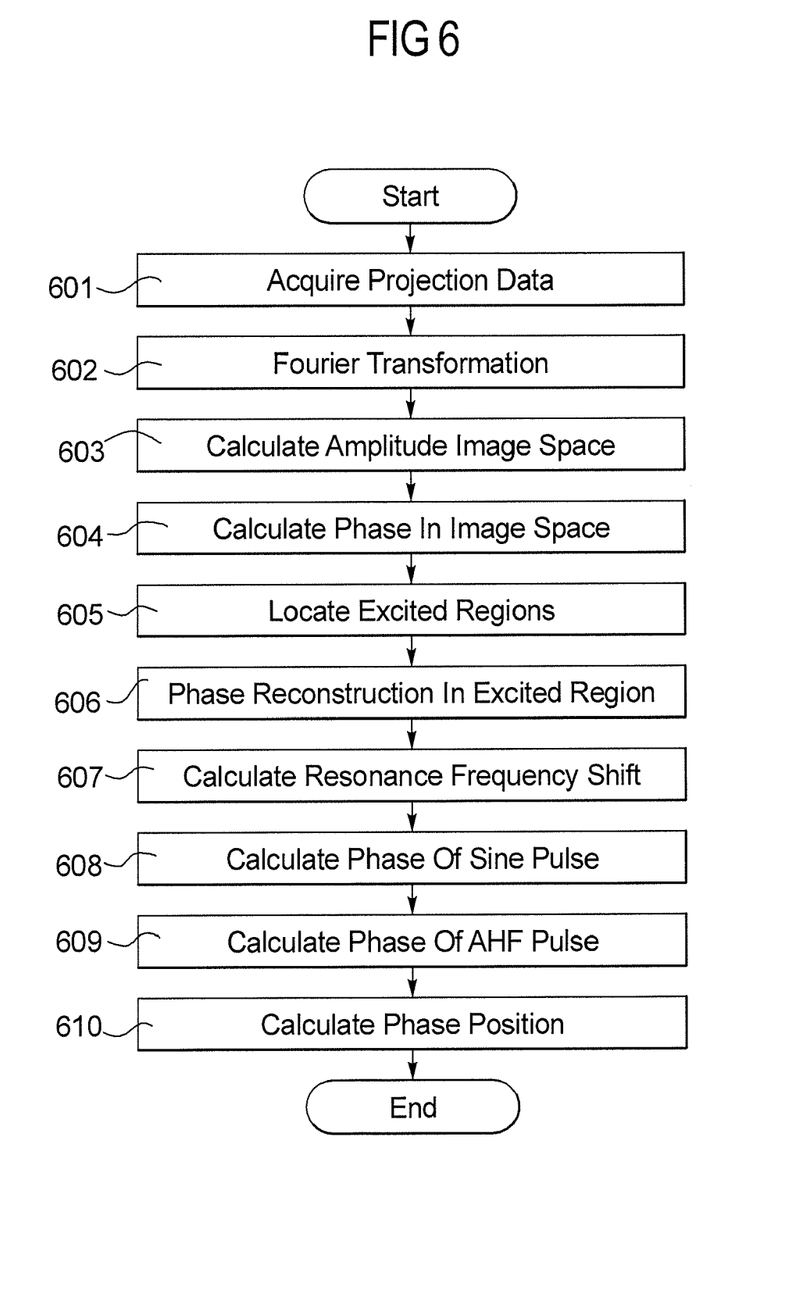
FIG. 6 is a flowchart that schematically represents the determination of an induced phase position from acquired magnetic resonance signals.

Acquired projection data are accessed in a first Step 601 in FIG. 6. These projection data are, for example, the magnetic resonance signals in k-space that were acquired (as illustrated in FIG. 5) after three different echo times $TE_1$, $TE_2$ and $TE_3$ (identified with reference character 511, 519 or, respectively, 527 in FIG. 5). For example, the acquired magnetic resonance signals can be stored on a data medium for a later processing; however, they can also be processed directly after their acquisition. In the example cited here, a frequency coding has only occurred in the axial (z-) direction; projection data thus exist with regard to the x- and y-direction. A Fourier transformation of the data into image space (image domain) follows in Step 602. For example, a one-dimensional Fourier transformation is thus implemented in the readout direction, after which three data sets $i_n$ exist in image space. The image space in this example extends one-dimensionally along the z-axis. The index n can assume the values 1, 2 and 3 and designates the magnetic resonance signals that were acquired after the sinc excitation, the first adiabatic excitation or, respectively, the second adiabatic excitation.

An amplitude in image space is calculated in Step 603. The amplitude in image space is given by $I_n = |i_n|$. In a next Step 604, the phase of the acquired magnetic resonance signals in image space is calculated. For example, this can ensue with the following equation.

$$\phi_n = a\tan 2(i_n) \qquad (1)$$

The phases $\phi_1$, $\phi_2$ and $\phi_3$ of the acquired magnetic resonance signals are thus known. It is noted that the amplitude I and the phase $\phi$ are dependent on the axial position z, wherein this dependency is not explicitly shown here for of clarity. Excited regions are located in a next Step 605. Given a radiation of an excitation pulse to slew the magnetization, all regions of a slice are normally not uniformly excited. Only the excited regions normally deliver a detectable magnetic resonance signal. For example, excited regions can thus be identified by location of signal intensities that lie above a predetermined threshold. Excited regions are advantageously discovered using the signal intensity in the image data $i_2$ or $i_3$.

This is in particular advantageous since the phase of a magnetic resonance signal can often not be determined or, respectively, is meaningless for unexcited regions.

In a next Step 606, a phase reconstruction ensues in the excited region. The implementation of the phase reconstruction (which is also designated as a "phase unwrapping") is particularly advantageous in the excited region since there the phase of the magnetic resonance signal is determined. If the phase of the acquired magnetic resonance signals is calculated, the value range of the phase extends only between 0° and 360° or, respectively, −180° and +180°. For example, a jump from +180° to −180° then occurs given larger phase angles. Such jumps are discovered in the phase reconstruction that, for example, exceed a predetermined angle difference (for example 100°), and if necessary 360° are then added to a phase or subtracted from this at this jump. Phase unwrapping methods are known to those skilled in the art, and thus need not be described in detail herein.

After Step 606, the "measured" phases $\phi_1$, $\phi_2$ and $\phi_3$ exist. These phases of the acquired magnetic resonance data are respectively the sum of the phase that was induced by the respective radio-frequency excitation pulse and an additional phase that is caused by a resonance frequency shift. This additional shift of the phase normally acts from the radiation of the excitation pulse to the acquisition of the magnetic resonance signal. As was already explained using FIG. 5, this additional rotation is compensated due to the self-refocusing AFP pulses. This additional rotation of the phase in the first adiabatic excitation pulse thus occurs only during a time span $T_{AHP}/2$, wherein $T_{AHP}$ designates the duration of the AHP excitation pulse. Due to the different echo times $TE_2$ and $TE_3$ of the first or, respectively, second adiabatic excitation pulse, an additional rotation of the phase results due to the resonance frequency shift for the third acquired magnetic resonance signal, thus for the phase $\phi_3$. The measured phase can correspondingly be specified as follows:

$$\phi_1 = \phi_{SINC} + \Delta\omega_0 \cdot TE_1 \quad (2)$$

$$\phi_2 = \phi_{AHP} + \Delta\omega_0 \cdot TE_{AHP}/2 \quad (3)$$

$$\phi_3 = \phi_2 + \Delta\omega_0 \cdot (TE_3 - TE_2) \quad (4)$$

wherein $\phi_{SINC}$ means the phase induced by the sinc excitation pulse, and $\phi_{AHP}$ means the phase induced by the adiabatic half-passage excitation pulse. The resonance frequency shift $\Delta\omega_0$ is calculated in Step 607 from Equation (4). This results as $$\Delta\omega_0 = (\phi_3 - \phi_2)/(TE_3 - TE_2) \quad (5)$$

Because $\Delta\omega_0$ is now known, the phase $\phi_{SINC}$ can be calculated in a next Step 608 using $\Delta\omega_0$ and $TE_1$, for example according to Equation (2). Furthermore, the second phase $\phi_{AHP}$ can be calculated in a next Step 609 using $\Delta\omega_0$ and $TE_{AHP}$, for example according to Equation (3).

The phase position induced by the adiabatic excitation pulse can now be calculated in Step 610 as a relative phase in relation to the phase induced by the sinc excitation pulse. For example, the phase position can be determined by $\phi_r = \phi_{SINC} - \phi_{AHP}$. The phase of the magnetization that is induced by the sinc-shaped excitation pulse thereby corresponds to the phase position that refocusing pulses of a subsequent multi-echo imaging sequence should exhibit. Since the phase induced by the AHP pulse is known relative to the aforementioned phase, this relative phase can be compensated in order to also satisfy the CPMG condition in a subsequent multi-echo imaging sequence given excitation with AHP and AFP pulses. The phase of the refocusing pulses after adiabatic excitation can thus be offset, for example by the relative phase in relation to the phase of refocusing pulses given conventional sinc excitation. The use of an adiabatic excitation pulse in a multi-echo imaging sequence is thus enabled via the described method. In particular the advantages of a $B_1$-insensitivity and of a homogeneous exposure of the slice are connected with the advantages of the multi-echo imaging sequences, for example the fast acquisition of magnetic resonance signals.

However, no explicit calculation of $\phi_{SINC}$ and $\phi_{AHP}$ must ensue for implementation of the method; rather, the relative phase $\phi_r$ can also be directly calculated form equations (2) and (3):

$$\phi_r = \phi_{SINC} - \phi_{AHP} = \phi_1 - \Delta\omega_0 \cdot TE_1 - (\phi_2 - \Delta\omega_0 \cdot T_{AHP}/2) \quad (6)$$

Furthermore, it is to be noted that many of the steps described in FIG. 6 are optional, for example Steps 603 and 605. The features that were described in relation to the different embodiments can be combined in order to form new embodiments that are contained in the scope of the invention. Additional modifications are also conceivable within the scope of the invention. For example, the sequence of excitation pulses could be changed, for example given a use of two sinc-shaped excitation pulses or a variation of the time sequence. Adiabatic excitation pulses can also be used that comprise various combinations of AHP and AFP pulses. The phase determination by the acquisition of projection data in the x-direction and y-direction that is illustrated here has the advantage that it can be implemented quickly; however, a frequency or phase coding is also conceivable in order to determine phase positions resolved in the x-direction and/or y-direction.

In summary, the method and magnetic resonance system described herein make use of adiabatic excitation pulses, and allow the phase of the magnetization that is induced by these pulses to be compensated. This type of excitation can be used with multi-echo sequences. The advantages of an adiabatic slice-selective excitation (for example $B_1$-insensitivity) thus can be utilized for multi-echo imaging.

Although modifications and changes may be suggested by those skilled in the art, it is the intention of the inventor to embody within the patent warranted hereon all changes and modifications as reasonably and properly come within the scope of the inventor's contribution to the art.

I claim as my invention:

1. A method to determine a phase position of a magnetization caused by radiation of an adiabatic RF pulse into an examination subject, for acquisition of magnetic resonance signals from a slice of the examination subject, comprising the steps of:
    radiating an RF pulse of a first type into the examination subject and acquiring a first magnetic resonance signal from the examination subject;
    after radiating said RF pulse of said first type, radiating an adiabatic RF pulse into the examination subject, and acquiring a second magnetic resonance signal from the examination subject;
    from said first magnetic resonance signal, automatically electronically calculating a phase of a magnetization induced by the RF pulse of the first type, as a first phase, and from said second magnetic resonance signal, automatically electronically calculating a phase of a magnetization induced by the adiabatic RF pulse, as a second phase; and
    automatically electronically determining the phase position of the second phase in relation to the first phase.

2. A method as claimed in claim 1 comprising employing a sinc-shaped RF pulse as said RF pulse of the first type.

3. A method as claimed in claim 1 comprising employing an adiabatic half-passage pulse as said adiabatic RF pulse.

4. A method as claimed in claim 3 comprising radiating said adiabatic half-passage pulse as a non-slice-selective RF pulse.

5. A method as claimed in claim 1 comprising radiating said adiabatic RF pulse as two adiabatic full-passage pulses.

6. A method as claimed in claim 5 comprising radiating a slice selection gradient, and radiating said adiabatic full-passage pulses in the presence of said slice selection gradient.

7. A method as claimed in claim 1 comprising:
radiating an additional adiabatic RF pulse into the examination subject and acquiring a third magnetic resonance signal from the examination subject; and
calculating said first phase and said second phase using said first, second and third magnetic resonance signals.

8. A method as claimed in claim 7 comprising acquiring said second and third magnetic resonance signals with different echo times.

9. A method as claimed in claim 8 comprising calculating said first phase and said second phase by calculating a resonance frequency shift based on said different echo times and the respective phases of the acquired second and third magnetic resonance signals.

10. A method as claimed in claim 1 comprising configuring said adiabatic RF pulse to generate a spin echo signal.

11. A method as claimed in claim 1 comprising calculating at least one of said first phase or said second phase by a phase reconstruction in regions in which phase jumps of a predetermined magnitude are detected between adjacent data points.

12. A method as claimed in claim 11 comprising implementing said phase reconstruction only regions with a predetermined signal intensity in image space.

13. A method as claimed in claim 1 comprising applying a gradient magnetic field in an axial direction of the examination subject, and acquiring the magnetic resonance signals while said magnetic gradient is applied in said axial direction.

14. A method as claimed in claim 13 comprising determining the phase position for a plurality of axial positions in a slice of the examination subject from which said magnetic resonance signals are acquired.

15. A method as claimed in claim 1 comprising generating a rephrasing gradient and a pre-phasing gradient in an axial direction of the examination subject before acquisition of said first magnetic resonance signal.

16. A method as claimed in claim 1 comprising acquiring said first magnetic resonance signal as a gradient echo magnetic resonant signal.

17. A method as claimed in claim 1 comprising, after determining said phase position, radiating a multi-echo magnetic sequence into the examination subject, comprising at least one adiabatic RF pulse, and acquiring diagnostic magnetic resonance signals as a result of said multi-echo magnetic resonance sequence.

18. A method as claimed in claim 17 wherein said multi-echo magnetic resonance sequence comprises refocusing pulses, and automatically establishing a phase of said refocusing pulses dependent on said determined phase position.

19. A method as claimed in claim 18 comprising establishing said phase of said refocusing pulses in a frequency-dependent manner.

20. A method as claimed in claim 17 comprising employing a turbo spin echo sequence as said multi-echo magnetic resonance sequence.

21. A method as claimed in claim 17 comprising employing the determined phase position to satisfy a CPMG condition of said multi-echo imaging sequence.

22. A magnetic resonance system to determine a phase position of a magnetization caused by radiation of an adiabatic RF pulse into an examination subject, for acquisition of magnetic resonance signals from a slice of the examination subject, comprising:
a magnetic resonance data acquisition device configured to receive an examination subject therein, said data acquisition unit comprising an RF radiator and a control unit that operates said RF radiator to radiate an RF pulse of a first type into the examination subject and acquire a first magnetic resonance signal from the examination subject, and, after radiating said RF pulse of said first type, to radiate an adiabatic RF pulse into the examination subject, and acquire a second magnetic resonance signal from the examination subject; and
a computer configured to automatically calculate from said first magnetic resonance signal, a phase of a magnetization induced by the RF pulse of the first type, as a first phase, and to automatically calculate, from said second magnetic resonance signal, a phase of a magnetization induced by the adiabatic RF pulse, as a second phase, and to automatically determine the phase position of the second phase in relation to the first phase.

23. A magnetic resonance system as claimed in claim 22 wherein said control unit operates said RF radiator to radiate an additional adiabatic RF pulse into the examination subject and acquire a third magnetic resonance signal from the examination subject, and wherein said computer is configured to calculate said first phase and said second phase using said first, second and third magnetic resonance signals.

24. A non-transitory computer-readable medium encoded with programming instructions operate a magnetic resonance system to determine a phase position of a magnetization caused by radiation of an adiabatic RF pulse into an examination subject by an RF radiator of the magnetic resonance system, for acquisition of magnetic resonance signals from a slice of the examination subject in the magnetic resonance system, said medium being loadable into a computer system of the magnetic resonance system and causing said computer to:
operate said RF radiation to radiate an RF pulse of a first type into the examination subject and acquire a first magnetic resonance signal from the examination subject;
after radiating said RF pulse of said first type, operate said RF radiator to radiate an adiabatic RF pulse into the examination subject, and acquire a second magnetic resonance signal from the examination subject;
automatically calculate from said first magnetic resonance signal, a phase of a magnetization induced by the RF pulse of the first type, as a first phase, and automatically calculate, from said second magnetic resonance signal, a phase of a magnetization induced by the adiabatic RF pulse, as a second phase; and
automatically determine the phase position of the second phase in relation to the first phase.

* * * * *